(12) United States Patent
Arnold et al.

(10) Patent No.: US 7,460,895 B2
(45) Date of Patent: Dec. 2, 2008

(54) METHOD FOR GENERATING A NET ANALYTE SIGNAL CALIBRATION MODEL AND USES THEREOF

(75) Inventors: Mark A. Arnold, Iowa City, IA (US); Jonathon T. Olesberg, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 114 days.

(21) Appl. No.: 11/042,817

(22) Filed: Jan. 24, 2005

(65) Prior Publication Data

US 2006/0167348 A1 Jul. 27, 2006

(51) Int. Cl.
*A61B 5/1455* (2006.01)
*G01J 3/00* (2006.01)
*G12B 13/00* (2006.01)

(52) U.S. Cl. .............. 600/310; 600/316; 356/300; 250/252.1

(58) Field of Classification Search .......... 600/310, 600/316, 322, 323, 336; 702/19; 356/300; 250/252.1
See application file for complete search history.

(56) References Cited

U.S. PATENT DOCUMENTS

| 5,379,238 | A | * | 1/1995 | Stark ...................... 600/316 |
| 5,459,317 | A |   | 10/1995 | Small et al. |
| 5,708,957 | A |   | 1/1998 | Chuang et al. |
| 6,061,582 | A |   | 5/2000 | Small et al. |
| 6,341,257 | B1 | * | 1/2002 | Haaland ...................... 702/22 |
| 6,574,490 | B2 | * | 6/2003 | Abbink et al. .............. 600/316 |
| 6,697,654 | B2 | * | 2/2004 | Lorenz et al. ............... 600/310 |
| 2003/0050541 | A1 | * | 3/2003 | Wuori ......................... 600/316 |

OTHER PUBLICATIONS

Burmeister, Jason J. et al "Evaluation of Measurement Sites for Noninvasive Blood Glucose Sensing with Near-Infrared Transmission Spectroscopy" Clinical *Chemistry.* 1999;45:1621-1627.
Lorber, A., Faber, K., and Kowalski, B.R., "Net Analyte Signal Calculation in Multivariate Calibration" *Anal. Chem.*, 69, 8, 1620-1626, 1997.
Lorber, A., "Error propagation and figures of merit for quantification by solving matrix equations" *Analytical Chemistry*, 58 (1986) 1167-1172.
Photonics West presentation, Jan. 24-29, 2004; Brief overview given in the abstract.

* cited by examiner

*Primary Examiner*—Eric F Winakur
(74) *Attorney, Agent, or Firm*—Ballard Spahr Andrews & Ingersoll, LLP (57) ABSTRACT

A method for generating a net analyte signal calibration model for use in detecting and/or quantifying the amount of an analyte in a test subject. The net analyte signal can be generated by providing a set of in vivo infrared spectra for a test subject during a period in which an analyte concentration is essentially constant; calculating an optimal subspace of spectra that at least substantially describes all non-analyte dependent spectral variance in the in vivo spectra; providing a pure component infrared spectrum for the analyte; and calculating a net analyte signal spectrum from a data set comprising the optimal subspace spectra and the pure analyte spectrum. The net analyte signal calibration model can be used, for example, in measuring the concentration of analyte in a test subject, and/or for evaluating the analytical significance of an in vivo multivariate calibration model.

32 Claims, 9 Drawing Sheets

METHOD FOR GENERATING A NET ANALYTE SIGNAL CALIBRATION MODEL AND USES THEREOF

The invention described in the foregoing specification has been developed in part with funds received from the National Institute of Diabetes and Digestive and Kidney Diseases of the National Institutes of Health under grant numbers DK-60657 and DK-02925. The United States Government may have certain rights under this invention.

FIELD OF THE INVENTION

The present invention relates generally to the field of in vivo spectroscopic analysis of a test subject and more particularly to a method for generating an in vivo net analyte signal calibration model and methods for the use thereof.

BACKGROUND OF THE INVENTION

Diabetes is one of the fastest growing diseases today. The World Health Organization estimates that 177 million people worldwide currently have diabetes and this number is projected to increase to more than 370 million people by the year 2030. The costs associated with diabetes, including premature death, pain and suffering, and increased financial burdens. These costs are directly related to the medical complications associated with chronic hyperglycemia. Early detection and maintaining a tight glycemic control are paramount to controlling the costs of the diabetic epidemic.

The cornerstone of tight glycemic control is frequent glucose monitoring, where blood glucose concentrations are measured to help administer proper levels of insulin and maintain euglycemic conditions. To this end, glucose sensing technology has advanced considerably in recent years to provide tools for home glucose monitoring and establishing opportunities for tight glycemic control. The current conventional determination of blood glucose is a routine invasive procedure typically performed several times a day. In general, this procedure involves the taking of a small blood sample and evaluating the level of glucose in the sample. Common instruments used for this use the enzyme glucose oxidase to convert glucose and oxygen to gluconic acid and hydrogen peroxide. The level of hydrogen peroxide is then measured by spectroscopic or electrochemical means which is reflective of the starting glucose concentration.

While these daily measurements provide a diabetic patient with the ability to self-monitor and thus better control blood glucose levels, they are not without drawbacks. In particular, the taking of blood samples several times daily can be very painful and expose the patient to elevated risks of infection. Moreover, these methods are not suitable for providing continuous blood glucose measurements. Thus, for example, during the night, a patient must either be awakened periodically for testing or else run the risk that glucose levels will drop dangerously low while they sleep.

Non-invasive optical sensing of an analyte, such as glucose, has been proposed as an approach for frequent and painless measurement of glucose in diabetics. However, to date, all reported attempts to measure glucose non-invasively have involved collecting spectra from a human and then using a classical statistical multivariate calibration technique to correlate variations in the spectral information to blood glucose concentrations. These statistical techniques rely on regressions to statistically correlate spectral variances to an artificially assigned glucose concentration. Thus, these measurements are not necessarily based on actual analyte specific spectral features. Further, these statistical methods fail to provide direct evidence that the assigned concentration predictions from the multivariate calibration models are actually based on glucose specific spectral information. Moreover, in some cases the in vivo spectral signature for a physiological analyte can be smaller than many weakly or partially correlated spectral variations, making the use of the conventional statistical methods very difficult.

Therefore, in view of the foregoing, there exists a need for an in vivo calibration method that can identify analyte specific spectral information. Further, there is also a need for a non-invasive method of measuring the concentration of an analyte in a test subject. Moreover, there is also a need for a method for evaluating the analytical significance of the classical statistical multivariate calibration models.

SUMMARY OF THE INVENTION

The present invention is based, in part, upon a method for generating an in vivo net analyte signal calibration model and methods for the use thereof.

In a first aspect, the present invention provides a method for generating a net analyte signal calibration model for use in detecting an analyte in a test subject. In accordance with this aspect, the method comprises providing a set of in vivo infrared spectra for a test subject during a period in which an analyte concentration is essentially constant; calculating an optimal subspace of spectra that at least substantially describes all non-analyte dependent spectral variance in the in vivo spectra; providing a pure component infrared spectrum for the analyte; and calculating a net analyte signal spectrum from a data set comprising the optimal subspace spectra of and the pure analyte spectrum. In one aspect, the net analyte signal spectrum is capable of identifying one or more in vivo spectral features specific to the analyte.

In a second aspect, the present invention provides a method for non-invasively measuring the concentration of an analyte in a test subject. In accordance with this aspect, the method comprises identifying a test subject in need of having an analyte concentration measured; providing an in vivo net analyte signal calibration model for the test subject; providing an in vivo infrared spectrum of the test subject; and calculating a predicted concentration of the analyte in the test subject from a data set comprising the net analyte signal calibration model and the in vivo infrared spectrum of the test subject.

In a third aspect, the present invention provides a method for evaluating the analytical significance of an in vivo multivariate calibration model. According to this aspect, the method comprises providing an in vivo multivariate calibration spectrum or vector for an analyte in a test subject; providing an in vivo net analyte signal calibration vector for the test subject; and comparing the in vivo multivariate calibration vectors to the in vivo net analyte signal calibration model for an analytically significant similarity in at least one spectral feature.

In still another aspect, the present invention mentioned provides a net analyte signal calibration model produced by the method described above.

Additional aspects of the invention will be set forth, in part, in the detailed description, Figures and Claims which follow, and in part will be derived from the detailed description, or may be learned by practice of the invention. It is to be understood that both the foregoing general description and the following detailed description are exemplary and explanatory only and are not restrictive of the invention as disclosed.

DETAILED DESCRIPTION OF THE INVENTION

The present invention may be understood more readily by reference to the following detailed description, examples and figures and their previous and following description.

Before the present compositions, devices, and/or methods are disclosed and described, it is to be understood that this invention is not limited to the specific articles, devices, and/or methods disclosed unless otherwise specified, as such may, of course, vary. It is also to be understood that the terminology used herein is for the purpose of describing particular aspects only and is not intended to be limiting.

As used herein, the singular forms "a," "an" and "the" include plural referents unless the context clearly dictates otherwise. Thus, for example, reference to "a test subject" includes aspects having two or more such test subjects unless the context clearly indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term or phrase "net analyte signal" refers to the residual spectrum that is orthogonal to non-analyte dependent sources of spectral variance, including spectral variations related to chemical components within the sample matrix and to variations induced by the instrumentation or experimental environment. The net analyte signal can be calculated according to any conventional method such as that described in detail in A. Lober, Analytical Chemistry 59, 1167 (1986), the entire disclosure of which is hereby incorporated by reference in its entirety for all purposes.

As used herein, the term or phrase "net analyte signal calibration model" refers to a function used to predict analyte concentrations from subsequent sample spectra. Such models are derived from the net analyte signal, which is scaled to produce the proper concentration units when multiplied by values from the unknown spectrum.

As used herein, the term or phrase "substantially constant" or "essentially constant" concentration refers to less than a 20 % change in concentration, less than a 15 % change in concentration; less than a 10% change in concentration, less than 5 % change in concentration, less than a 2 % change in concentration, less than 1 % change in concentration, or even a 0 % change in concentration.

As used herein, the term or phrase "background spectra" refers to a subspace of spectra that describes at least a substantial number of baseline factors attributed to non-analyte dependent spectral variations in in vivo spectra of a test subject. To this end, in one aspect, a substantial number of baseline factors is the number of baseline factors that account for substantially or essentially all non-analyte dependent spectral variances. Thus, as used herein, substantially or essentially all can refer to at least greater than 80 % of the non-analyte dependent spectral variations, at least greater than 85 % of the non-analyte dependent spectral variations, least greater than 90 % of the non-analyte dependent spectral variations, at least greater than 95 % of the non-analyte dependent spectral variations, or even greater than 99 % of the non-analyte dependent spectral variations.

As used herein, the term or phrase "pure component spectra" refers to the spectra or spectrum of a pure analyte. Accordingly, in one aspect, pure component spectra can be obtained from a sample comprised of the analyte of interest dissolved in an aqueous buffer solution.

As used herein, the term or phrase "analytical significance" refers to the degree, likelihood, or probability that one or more spectral features in a first spectrum or set of spectra results from the same or similar spectral feature described in a second spectrum or set of spectra. In one aspect, the analytical significance can be evaluated by comparing the degree of overlap between a first and a second spectrum or set of spectra. To this end, in one aspect, the analytical significance can be quantified by determining the inner product defined by the overlap of the two spectra. Alternatively, the analytical significance can be quantified by determining the relative angle between the two spectra.

As used herein, the term or phrase "spectroscopy system" refers to, in one aspect, a system comprised of conventional components that can be used to irradiate a test subject with electromagnetic radiation and subsequently detect variations in the electromagnetic radiation resulting at least from an interface with the test subject. For example, in one aspect, a spectroscopy system can comprise a light source for providing electromagnetic radiation in a desired band of wavelengths and at a desired level of intensity. The system can further comprise an interface module for bringing the electromagnetic radiation to a test site of a test subject. Additionally, the spectroscopy system can further comprise an interferometer, detector, and suitable data processing capability for determining the spectrum of the electromagnetic radiation resulting at least in part from the interface of the electromagnetic radiation with the test subject. As one of ordinary skill in the art will appreciate upon practicing the invention disclosed herein, other spectrometer designs could also be used in place of this described exemplary interferometer based spectroscopy system. For example, spectroscopy systems according to the present invention can also include detector array multiplex systems and dispersive systems.

In one aspect, an exemplary spectroscopy system according to the present invention can be configured to operate in the near infrared electromagnetic region, including radiation in the wavenumber range of from approximately 4000 cm$^{-1}$ to approximately 14500 cm$^{-1}$. To this end, the spectroscopy system can be configured to operate in additional wavenumbers of 5000, 5500, 6000, 6500, 7000, 7500, 8000, 8500, 9000, 9500, 10000, 10500, 11000, 11500, 12000, 12500, 13000, 13500 and 14000 cm$^{-1}$ and any range derived from these values. In still another aspect, and for example when used in an aqueous environment, like the human body, the spectroscopy system can operate in the so-called combination spectral range of the near infrared spectrum over a wavenumber range from approximately 4000 cm$^{-1}$ to approximately 5000 cm$^{-1}$. As one of ordinary skill in the art will appreciate, spectral features in the combination spectral range originate from the combination of stretching and bending vibrational modes associated with C—H, O—H, and N—H chemical bonds within the molecules in the sample matrix. In still another aspect, and again for exemplary aqueous samples, the spectroscopy system can operate in the so-called first overtone spectral region of the near infrared spectrum over the wavenumber range from approximately 5500 cm$^{-1}$ to approximately 6500 cm$^{-1}$. Spectral features in this first overtone spectral range correspond to the first overtone of C—H chemical bonds within these sample molecules.

In an alternative aspect, the spectroscopy system can be configured to operate in the mid infrared electromagnetic region, including radiation in the wavenumber range from approximately 300 cm$^{-1}$ to approximately 4000 cm$^{-1}$. To this end, the spectroscopy system can be configured to operate in additional sub-ranges within the wavenumber bands of 500, 1000, 1500, 2000, 2500, 3000, and 3500 cm$^{-1}$ and any range derived from these values. It should also be understood that for both near infrared and mid infrared spectroscopy measurements, it is not required by the invention that the wavelength range used be a single contiguous range of wavenumbers. For example, in still another aspect, a plurality of different segments of shorted wavenumber ranges can be used.

As one of ordinary skill in the art will appreciate, the desired configuration of the spectroscopy system will be dependent on the particular analyte under investigation. For example, in one aspect where the analyte is glucose, an exemplary spectroscopy system can comprise a conventional Fourier transform infrared (FTIR) spectrometer configured to operate in the NIR spectral range from approximately 4000 cm$^{-1}$ to approximately 5000 cm$^{-1}$. The system according to this aspect can further comprise a 50 W tungsten-halogen bulb with an integrated, gold coated reflector used as a broadband light source. After collimation, incident light from the source can enter a Michaelis interferometer and is modulated accordingly. A custom fiber optic interface can be provided to bring this modulated light from the interferometer to the test subject and to couple the light transmitted through the subject to an external detector. A 1 mm diameter solid-core low-hydroxy silica fiber terminated with a 4 mm diameter sapphire ball lens can be used for light delivery to the test subject. Transmitted light through the test subject can then be collected using a second ball lens into another solid-core fiber. Collected light can then be coupled using an aspheric lens pair onto a two-stage thermoelectrically-cooled extended-wavelength InGaAs detector with a 2.6 micron (3846 cm$^{-1}$) cutoff. The current output from the detector can be converted to a voltage signal using a low-noise, variable gain, transimpedance amplifier, the output of which can be connected to a set of electronics to record the detector signal by a computer as a function of time. The corresponding time domain spectrum can then be converted to a frequency domain spectrum by the well-known Fourier transformation. This frequency domain spectrum can then be used for all subsequent data processing, such as building and testing calibration models as described herein.

In addition to the exemplary transmission spectrum spectroscopy system described above, it should also be understood that in another aspect of the instant invention, analytical special data can be collected as a diffuse reflectance spectrum or a transflectance spectrum. In still another aspect, it is also possible for the methods of the instant invention to be used with total attenuated reflectance spectra and spectral collected by photoacoustic configuration. To this end, the present invention can be used in connection with any spectral data, irrespective of the nature and configuration of the spectroscopy system from which it was obtained.

As briefly discussed above, in a first aspect, the present invention provides a method for generating a net analyte signal calibration model. The calibration model can, in one aspect, be used in detecting an analyte in a test subject. The method comprises obtaining a set of in vivo spectra for a test subject during a period in which an analyte concentration is substantially constant. Background spectra is then calculated by determining an optimal subspace of spectra that at least substantially describes all non-analyte dependent spectral variance in the in vivo spectra. The net analyte signal spectrum of the pure analyte can then be calculated from a data set comprising the background spectra and the pure component spectrum of the analyte. To this end, in one aspect, the net analyte signal spectrum is capable of identifying at least substantially all unique features of the analyte spectrum compared to the background spectra. This process results in a unique and characteristic spectral signature of the analyte in the tested in vivo environment.

The in vivo spectra of a test subject can be obtained by either transmission, diffuse reflectance, transflectance, attenuated total reflectance, or photoacoustic measurement techniques over the spectral range of interest that favors the selective measurement of the selected analyte. To this end, in one aspect, a spectroscopy system as described herein can be used to obtain the in vivo spectra. In still another aspect, the spectroscopy system can be configured to operate in the near infrared (NIR) and mid infrared (MIR) regions as described herein.

In one aspect, suitable NIR electromagnetic radiation for use in the present invention coincides with the absorbance bands of the analyte of interest being measured. For example, if the analyte is glucose, the appropriate NIR bands are located in the regions of approximately 5000 cm$^{-1}$ to approximately 4000 cm$^{-1}$ and/or approximately 6500 cm$^{-1}$ to approximately 5500 cm$^{-1}$.

Since the in vivo spectra obtained and used in the method of the present invention can be either transmittance spectra, reflectance spectra, transflectance, attenuated total reflectance, or photoacoustic, considerable latitude is also available in the manner and location in which the NIR radiation impinges on the test subject. For example, if transmitted NIR radiation is being measured, the NIR radiation can, in one aspect, impinge on a relatively thin, fleshy area of a test subject, such as, for example, the fleshy webs between the fingers or toes or the ear lobe of a human test subject. If reflectance spectra are to be used, the sampling site can, in another aspect, be characterized by high blood flow close to the surface, such as, for example, the ventral surface of the wrist.

The source of NIR radiation used in the present invention can be such that it is disposed directly against the surface of the test subject. For example, a small halogen lamp could be used. Alternatively, the source can be physically remote from the test subject. In the latter case, it can be advantageous, although not necessary, to guide the NIR radiation to the desired irradiation sampling site on the surface of the test subject, for example, by means of optical fibers.

The data concerning the transmitted or reflected NIR radiation is, in one aspect, collected using a detector. The specific nature of the detector is not critical, provided it is capable of detecting the pertinent wavelengths of light. An example of a suitable detector for collection of an absorbance spectrum is a combination of a dispersive element, e.g., a grating or prism, and an optical multi-channel analyzer sensitive to NIR radiation. For example, in a case where the data to be collected is a single beam or reflectance spectrum, an absorbance spectrum or an interferogram, a suitable detector can comprise a combination of an NIR interferometer and a photon counting detector such as a solid state indium antimonide detector. To this end, it should be understood that there are many commercially available detectors that can be used, depending on the exact wavelengths of electromagnetic radiation being measured. For example, in many cases multiple detectors are available for any particular wavelength range and detector can be characterized by its detectivity and, ultimately, the resulting spectral signal-to-noise ratio.

The positioning of the detector relative to the test subject will depend both on the nature and size of the detector and the environment in which the measurement is being taken. For some purposes, it will be desirable to have the detector physically separated from the test subject, both because of detector size and to maximize detector performance by providing the detector with a stable environment. It will therefore generally be advantageous to guide the transmitted or reflected NIR radiation to the detector, for example using optical fibers.

Depending on the instrumentation selected, the data concerning the transmitted or reflected radiation is collected as either a single-beam spectrum, a reflectance spectrum, an absorbance spectrum or an interferogram. In each case, the collected data with essentially no change in analyte concentration are then used to calculate a set of background spectra or factors. These background spectra, as described herein, represent a subspace of spectra that at least substantially describes all non-analyte dependent spectral variances in the in vivo spectra. In one aspect, an optimal subspace that incorporates the primary systematic variations in a set of spectra can be obtained by performing a conventional principle component analysis.

As one of skill in the art will appreciate, the primary systematic variations in a set of spectra can be captured by one or more baseline factors that depend on the particular sample or test subject under investigation and/or the noise characteristics of the spectroscopy system. For example, the spectral variations described by the principle components in a set of spectra can, in one aspect, be due to tissue state variations induced by the pressure of the clamp (e.g., changes in water and protein content), variations in test subject physiology, and/or instrumental drift.

The background spectra representing the subspace at least substantially describing all of the spectral variations can, in one aspect, be calculated by concatenating the set of in vivo spectra as columns of a matrix:

$$B = [b_1 \ldots b_n]$$

Where B is the matrix of background spectra $b_1 \ldots b_n$. These spectra are then mean centered using the average background spectrum, $b_{avg}$:

$$B' = B - b_{avg}$$

A singular value decomposition calculation can then be used to obtain a set of orthogonal spectra or factors that describe the systematic and nonsystematic variations in the in vivo spectra obtained during a period when the analyte concentration is held essentially constant. Additional processing calculations can utilize the most significant factors that characterize the systematic spectral variations within this set of background spectra.

Using conventional mathematical models known to one of ordinary skill in the art, the net analyte signal for the particular analyte under investigation can then be obtained by removing all significant background factors, as described above, from the pure component spectrum of the analyte. This step produces that component of the analyte pure component spectrum that is orthogonal, or unique, compared to the non-analyte in vivo spectral variance accounted for within the background factors.

For example, and without limitation, the net analyte signal can in one aspect be calculated according to the following mathematical model:

$$U_{orth} = U - \frac{U \cdot V}{V \cdot V} V$$

Where $U_{orth}$ represents the component of vector U that is orthogonal to vector V. In this example, U represents the pure component spectrum of the analyte and V represents the factors that encode at least substantially all non-analytical spectral variance in the in vivo spectra. In this expression $U_{orth}$ corresponds to the net analyte signal. To obtain the net analyte signal of the pure component spectrum, the corresponding values are substituted into this equation. To this end, as indicated by the Examples appended hereto, the resulting net analyte signal for a particular analyte under investigation can be used as a calibration model for use in detecting and/or quantifying the presence of an analyte in a test subject from in vivo spectra.

It should be understood that the method of the present invention is not limited to any one particular analyte or group of analytes. To this end, in one aspect the analyte can be any physiological chemical having a functional group and/or chemical bond capable of providing an identifiable spectral signature or feature when irradiated with NIR or MIR radiation. In one aspect, the functional group and/or chemical bond can be C—H, N—H, O—H, or any combination thereof. Specific and non-limiting examples of suitable analytes for use in connection with the instant invention include glucose, urea, lactate, triglyceride, protein, cholesterol, and ethanol. In one aspect, the analyte is glucose. In still another aspect, the analyte is urea.

The test subject to which the method of the invention can be applied is similarly not limited to any one particular test subject. To this end, the test subject can be any living or deceased living organism containing a minimum concentration of an analyte as described above. For example, in one aspect, the test subject can be a plant. According to this aspect, in one example, the methods of the instant invention could be used to non-invasively detect and/or determine the sugar level within a fruit in order to assess the ripeness of the fruit and/or its readiness for harvesting. Alternatively, in another aspect, the test subject can be an animal. The animal can be mammalian or non-mammalian. The animal can also be a cold-blooded animal, such as a fish, a reptile, or an amphibian, or the animal can be a warm-blooded animal, such as a human, a farm animal, a domestic animal, or a laboratory animal, as further described herein. Further, the test subject can also be a cellular or microbial species. To this end, in still another aspect, the test subject can comprise a cluster of cells or microbial species.

As one of ordinary skill in the art will appreciate, it is further possible, although not required, to pre-process and/or manipulate the spectra before implementing the above described procedure. For example and without limitation, by any known convention method, spectra can be mean-centered, scaled, windowed, weighted, filtered, or even linearized without adversely impacting the methods of the instant invention. To this end, if desired, any one or more pre-processing or manipulation step set forth above can be used to, for example, improve performance or enhance identification.

A scaled calibration spectrum or calibration vector for the net analyte signal calibration model can be generated by the following equation:

$$\beta_k = \frac{NAS_k}{\|NAS_k\|^2}$$

Where $\beta_k$ is the calibration vector for analyte k and $NAS_k$ is the net analyte signal vector for analyte k as described above.

In a further aspect, the present invention provides a method for non-invasively predicting the concentration of an analyte in a test subject. According to this method, the predicted concentration of the analyte can be calculated from a data set comprising a net analyte signal calibration model for the analyte in the test subject and the in vivo spectrum of the test subject.

In one aspect, the net analyte signal calibration model can be provided, for example, from a database of net analyte signal calibration models. Alternatively, the net analyte signal calibration model can be provided by generating the net analyte signal calibration model in accordance with the methods set forth herein.

The in vivo spectrum of the test subject can, in one aspect, be provided from a database or catalogue of previously obtained spectra for the test subject. Alternatively, the in vivo spectrum can be provided by any conventional method, including irradiating the test subject with the appropriate range of wavelengths or wavenumbers of radiation followed by the appropriate detection as described herein.

Once the net analyte signal calibration model and the in vivo spectrum for the test subject have been provided, the concentration values for an analyte can be empirically predicted according to the following expression:

$$C_k = \frac{\beta_k \cdot A}{l} + \overline{C}_b$$

Where $C_k$ is the concentration of analyte k, $\beta_k$ is the calibration vector from the net analyte signal, A is the absorbance spectrum measured for the sample, $\lambda$ is the optical path length for the sample as measured by any known conventional method, and $C_b$ is the mean concentration of the analyte in the set of background spectra used to generate the net analyte signal. This same basic equation can be used in connection with all other types of spectra, including single-beam spectra and spectra collected in reflectance or transflectance optical geometries.

In still another aspect, the present invention provides a method for evaluating the analytical significance of an in vivo multivariate calibration model. According to this aspect, the method comprises providing an in vivo multivariate calibration spectrum for an analyte in a test subject; providing an in vivo net analyte signal calibration model for the test subject; and then comparing the in vivo multivariate calibration spectrum to the in vivo net analyte signal calibration model. A positive comparison of these calibration spectra indicates that the multivariate calibration model is, at least partially, composed of spectral information originating from the analyte of interest. In an ideal situation, the two calibration models will be identical, which indicates that the multivariate calibration is composed only of analyte specific information and no spurious concentration correlations are responsible for the calibration function in the case of the statistically based multivariate calibration process.

The method for evaluating the analytical significance of an in vivo multivariate calibration model can be used in connection with a calibration model generated for any analyte described herein as well as any test subject described herein. Furthermore, in one aspect, the multivariate calibration model is a partial least squares calibration model. In still another aspect, the multivariate calibration model is a principle component regression model.

The analytical significance can be determined by any conventional means of comparing two or more calibration vectors or spectra. For example, in one aspect, the analytical significance can be evaluated by comparing the degree of overlap between a first and a second spectrum or set of spectra. To this end, the analytical significance can be quantified by determining the inner product defined by the overlap of the two spectra. Alternatively, the analytical significance can be quantified by determining the relative angle between the two spectra.

A further aspect of the present invention provides a device for performing any one or more methods of the instant invention. A device according to this aspect can be used on any test subject in connection with any analyte, as both are described herein. In one aspect, the device is for generating a net analyte signal calibration model. In an alternative aspect, the device is for measuring the concentration of an analyte in a test subject. In still another aspect, the device is for evaluating the analytical significance of of an in vivo multivariate calibration model. It is further contemplated that a device according to the instant invention can be hand held and/or otherwise configured for portable use.

In one aspect, a device according to the instant invention can be configured for the non-invasive, quantitative detection of an analyte in a living or deceased living organism. Such an apparatus can comprise any one or more components of a spectroscopy system as described herein. For example, in one aspect, the device comprises a source of electromagnetic radiation for irradiating a test subject with electromagnetic radiation such that the radiation is transmitted through or reflected from the exterior surface of the test subject and is available for detection. The device can further comprise an interface module for bringing the electromagnetic radiation to a test site of a test subject. Additionally, the device can also comprise an interferometer, detector, and suitable data processing capability for determining the spectrum of the electromagnetic radiation resulting at least in part from the interface of the electromagnetic radiation with the test subject. To this end, as one of ordinary skill in the art will appreciate upon practicing the invention disclosed herein, any configuration of a device can be utilized provided the device contains the components necessary to detect and collect spectral data in a transmission, diffuse reflectance, transflectance, attenuated total reflectance, or photoacoustic configuration.

In another aspect, the spectral data collected by the device can be transferred to a computer readable storage medium from whence it can be read by a computer processor and processed in accordance with a programmed instruction to perform a desired function or mathematical expression on the recorded data. A suitable computer processor for use in this application can include any commercially available microprocessors.

The computer program used to process data obtained and stored in the device can be written in any programming language capable of, for example, performing a Fourier transform. For example, a program written in Fortran could be employed to perform the data analysis described in the Examples herein.

It is further envisioned that stored data can be recalled by the computer processor and operated under a second set of programmed instructions in order to apply a predetermined mathematical model to the data. For example, if a net analyte signal calibration model is generated and stored in the device, it is envisioned that in another aspect, that data can be recalled by a processor at some later time and operated under a set of programmed instructions in order to apply a subsequent and predetermined mathematical model that will calculate, for example, a predicted analyte concentration.

A device according to the instant invention can also comprise one or more means for reporting a result of a calculation or other mathematical expression, such as the calculation of a predicted analyte concentration. Non-limiting examples of a reporting means include a digital display panel, transportable read/write magnetic media such as computer disks and tapes which can be transported to and read on another machine, and printers such as thermal, laser or ink-jet printers for the production of a printed report.

In still another aspect, the present invention provides the net analyte signal calibration model produced by the methods described herein.

EXPERIMENTAL

The following examples and experimental data are put forth so as to provide those of ordinary skill in the art with a complete disclosure and description of how, in one aspect, a net analyte signal calibration model can be generated, used and/or evaluated. These examples are intended to be purely exemplary of the invention and are not intended to limit the scope of what is encompassed within the spirit and scope of the invention. Efforts have been made to ensure accuracy with respect to numbers (e.g., amounts, temperature, etc.) However, some errors and deviations should be accounted for.

Adult male Sprague Dawley rats were used as an animal test subject in the following examples. Retired breeder rats weighing more than 400 g were used. The rats were anesthetized using sodium pentobarbital for the surgical preparation. Anesthesia was maintained during the course of the procedure by administering chloralose. A catheter was placed in the right femoral vein for the infusion of glucose saline, and anesthetic during the experiment. The right femoral artery was cannulated to provide access to the arterial blood stream.

The rats were fasted overnight prior to the clamp experiments. After anesthetization, rectal temperature and pulse-oximetry probes were inserted to monitor animal temperature, pulse rate, and oxygenation during the cannulation procedure, which was performed on a heated surgical station. After surgery, the animal was transferred to the spectroscopy station. Animal temperature was maintained at 38.0° C. using a closed-loop temperature controller. Pulse rate and oxygenation were monitored continuously. Supplemental oxygen was provided to the animal at a rate of approximately 1 L/min.

Test spectra were collected using a Nicolet Nexus FTIR spectrometer. Spectra were collected continuously through a skin fold on the rat's back. A 50 W tungsten-halogen bulb with an integrated, gold coated reflector was used as a broad-band light source. A custom fiber optic interface was used to bring light from the spectrometer to the animal and to couple the transmitted light to an external detector. A 1 mm diameter solid-core low-OH silica fiber terminated with a 4 mm diameter sapphire ball lens was used for light delivery to the skin fold. Transmitted light was collected using a second ball lens into another solid-core fiber. The collected light was then coupled using an aspheric lens pair onto a two-stage thermo-electrically-cooled extended-wavelength InGaAs detector with a 2.6 micron cutoff. The current output from the detector was converted to a voltage signal using a low-noise, variable gain, transimpedance amplifier, the output of which was connected to the external detector port of the spectrometer. Spectra were recorded as 60 s averages with 16 $cm^{-1}$ (8 nm) spectral resolution.

After the fiber-optic interface was attached to the animal, spectra were colleted for approximately 3 hours while the blood glucose levels were held constant. During this time, isotonic saline was infused into the venous line at a rate of 2 mL/hr, which is the average fluid intake rate for a rat of the size used in this experiment. After a sufficient set of baseline spectra were collected, the saline infusion was replaced with an infusion of a 50% glucose solution at a rate of 2 mL/hr for 2 hours. After that, the glucose infusion was stopped and saline infusion resumed. The overall infusion rate was constant over the course of the experiment.

The fiber optic-interface was located across a skin fold on the animals back, near the shoulders. After initial placement, the interface was not moved during the experiment, except for a 45 minute period during which it was repositioned between each scan. The average thickness of the skin fold during the course of the experiment was approximately 1.5 mm.

Figure 1:
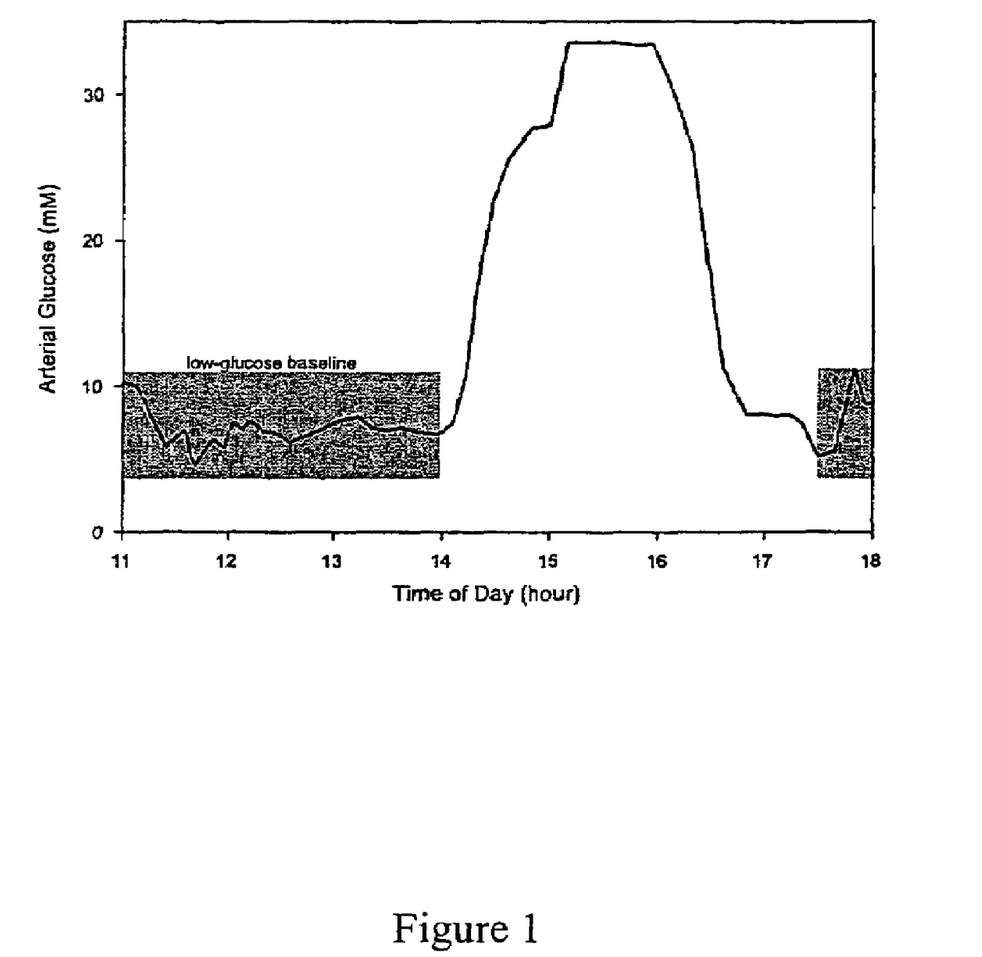
FIG. 1 shows the time profile of arterial glucose concentration in the test subject of Example 1.

Blood samples were collected from the arterial cannula at 5-15 minute intervals. Arterial glucose readings were measured using HemoCue® Glucose 201 Analyzer. When blood glucose values exceeded the functional range of the device (24 mM), the blood samples were diluted with saline. Calibrations were performed with a set of diluted and non-diluted blood samples within the functional range of the device to correct for a proportional error due to the reduction of hematocrit in the diluted samples. FIG. 1 shows the actual arterial glucose concentration in the rat over the course of the experiment.

EXAMPLE 1

Generation of an in vivo Net Analyte Signal Calibration Model for Glucose in a Lab Rat as Tested Above Using the data collected from the experimental procedure described above, an in vivo net analyte signal calibration model for glucose in the lab rat was generated. First, the time profile of arterial glucose concentration in the lab rat over the course of the experiment is depicted in FIG. 1. The lower, shaded regions on FIG. 1 indicate the times during the course of the experiment when the glucose concentration was held substantially constant and the times from which the obtained spectra were used to form the baseline background spectra (11:00-13:50 and 17:30-18:00). The latter set of shaded spectra were included in the background calculation of the baseline factors in order to correct for long term drift in the spectroscopy system. During the period from 13:00-13:45, the fiber optic clamp was repositioned on the animal between each scan in order to account for possible variations due to interface placement and tissue state variations in the baseline spectra.

A principle component analysis was then performed on the baseline spectra and it was determined that a set of nine baseline factors described the majority of the non-glucose systematic variations in the baseline spectra. This number of factors was chosen based on a visual inspection of the residuals after removing an increasing number of factors. These nine factors defined a subspace that contained the substantial majority of spectral variance observed in the baseline portion of the experiment.

Figure 2:
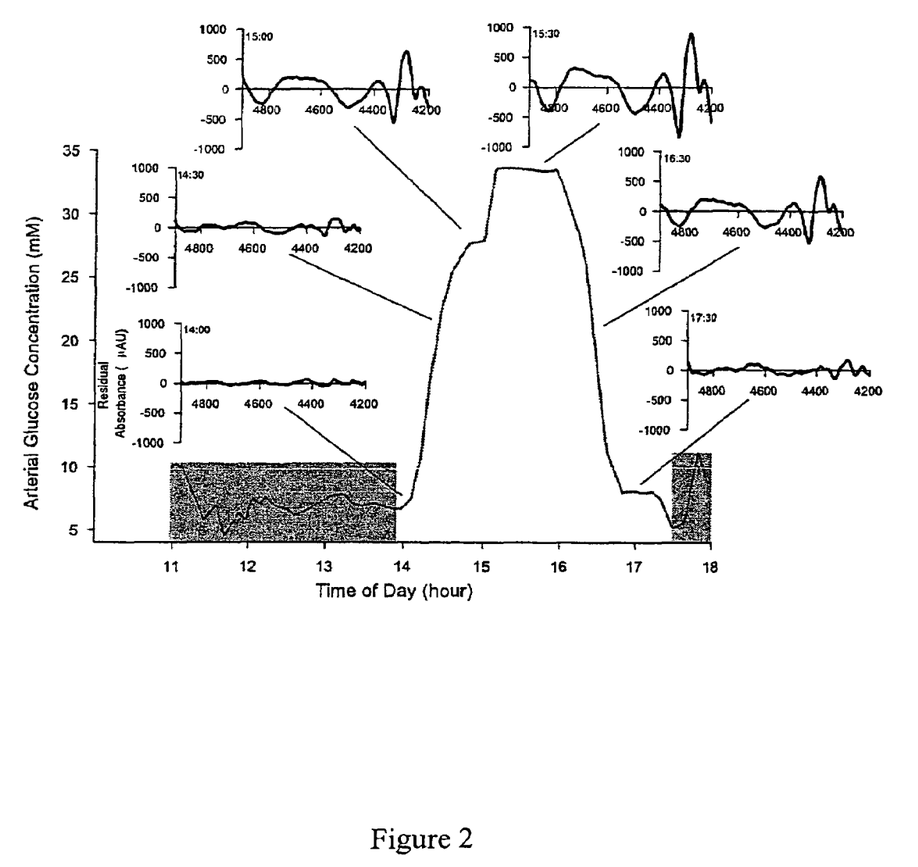
FIG. 2 shows the residual tissue spectra of Example 1 after the removal of baseline factors from selected points along the time profile depicted in FIG. 1.
Figure 3:
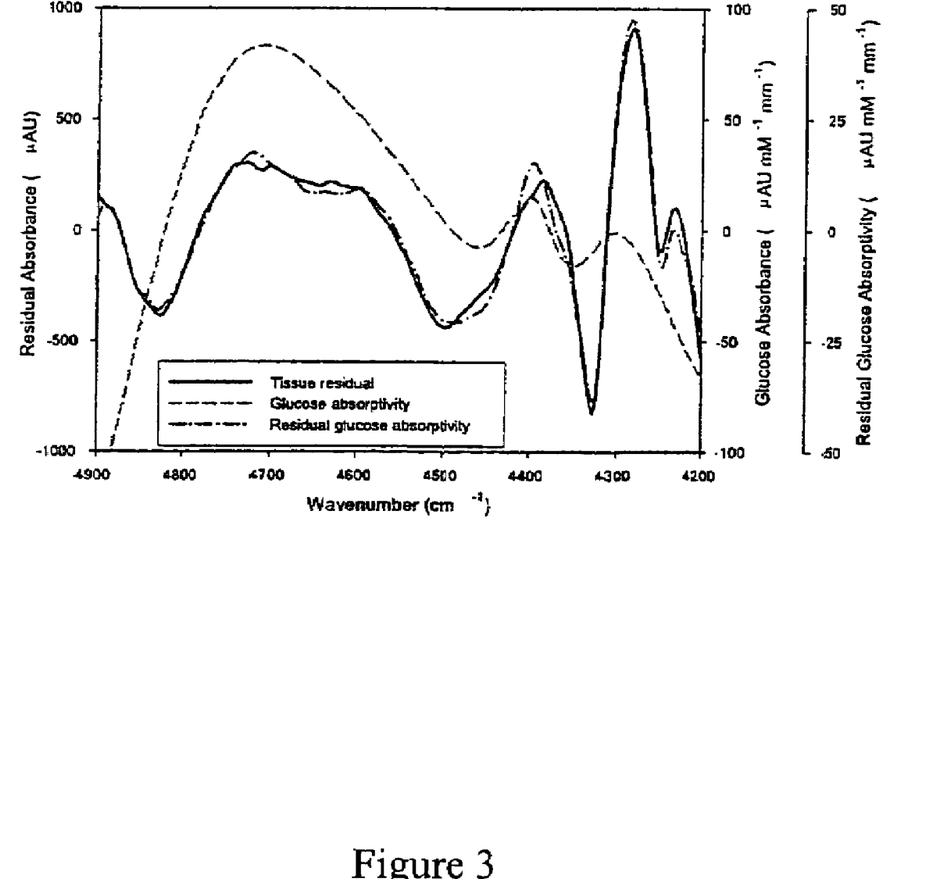
FIG. 3 shows the average residual tissue spectrum of FIG. 2 in comparison with the pure component spectrum of glucose and the net analyte signal of glucose as calculated in Example 1.

The subspace describing these nine factors was used to generate background spectra which were then removed from the in vivo spectra obtained at selected points throughout the experiment, including times when the concentration of glucose was elevated. The residual tissue spectra after the removal of the nine baseline factors are illustrated in FIG. 2. When these factors were removed from the spectra for which the animal's glucose concentration was elevated, significant residual structure remained. The average residual spectrum after the subtraction of the nine baseline factors is shown as the solid line in FIG. 3. The dashed line in FIG. 3 represents the pure component absorptivity spectrum of glucose. As illustrated, there was some similarity between the residual tissue spectra and the pure component spectra of glucose, both having peaks around 4700, 4400 and 4300 $cm^{-1}$.

The average residual tissue spectrum was then compared to the net analyte signal of glucose, which was obtained by similarly removing the nine baseline factors from the pure component spectrum of glucose. The net analyte signal of glucose is depicted on FIG. 3 as the dash-dot line. As illustrated, there was an increased similarity between the residual in vivo tissue spectra obtained during the time when the glucose concentration was elevated and the net analyte signal of the glucose. This similarity provides direct evidence of glucose specific spectral information present within the in vivo spectra.

EXAMPLE 2

Use of the Model to Measure a Predicted Concentration

The net analyte signal of glucose generated in Example 1 above was used to calculate predicted concentrations of glucose at selected periods during the course of the experimental procedure.

The glucose concentration was calculated using the following mathematical model:

$$C_{glucose} = \frac{\beta_{glucose} \cdot A}{l} + \overline{C}_b$$

Where $C_{glucose}$ is the concentration of glucose in the animal, $\beta_{glucose}$ is the glucose calibration vector from the net analyte signal, A is the absorbance spectrum measured for the rat skin, $\lambda$ is the optical path length, which is approximately 0.7 mm in this experiment, and $\overline{C}_b$(bar) is the mean concentration of glucose in the set of baseline spectra used to generate the net analyte signal. The average glucose concentration is ca., 7 mM for the baseline spectra used in this experiment.

Figure 4:
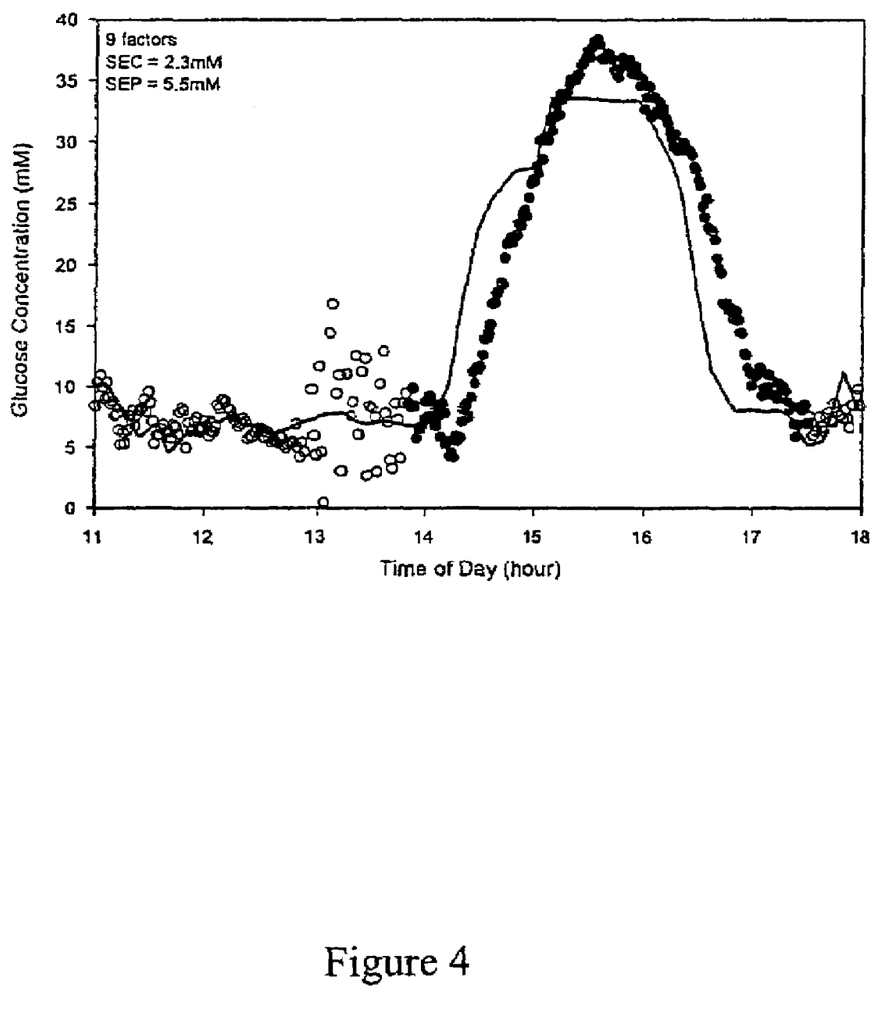
FIG. 4 shows the predicted glucose concentrations as calculated according to Example 2. The open circles represent predictions during the baseline periods, the solid circles represent predictions derived from non-baseline spectra and the solid line is the time profile of the arterial blood glucose concentration of FIG. 1.

The results of this calculation are indicated in FIG. 4, wherein the open circles represent the spectra used in the calculation of the background baseline factors and the solid circles are predictions for spectra not in the baseline set.

The significant scatter indicated in the period from 13:00-13:45 is due to added spectral variability caused by the repositioning of the optical fiber interface between scans. The predicted glucose concentrations closely followed the arterial glucose measurements indicated by the solid line with an approximate 15-20 minute delay that was to be expected due to the time required for an increased arterial concentration to result in a corresponding increase in tissue concentration.

EXAMPLE 3

Generation of in vivo PLS Multivariate Calibration Model

The net analyte signal of glucose generated in Example 1 was also used to evaluate the analytical significance of a classical partial least squares regression calibration model obtained from the same spectral data obtained in the experimental procedure.

Figure 5:
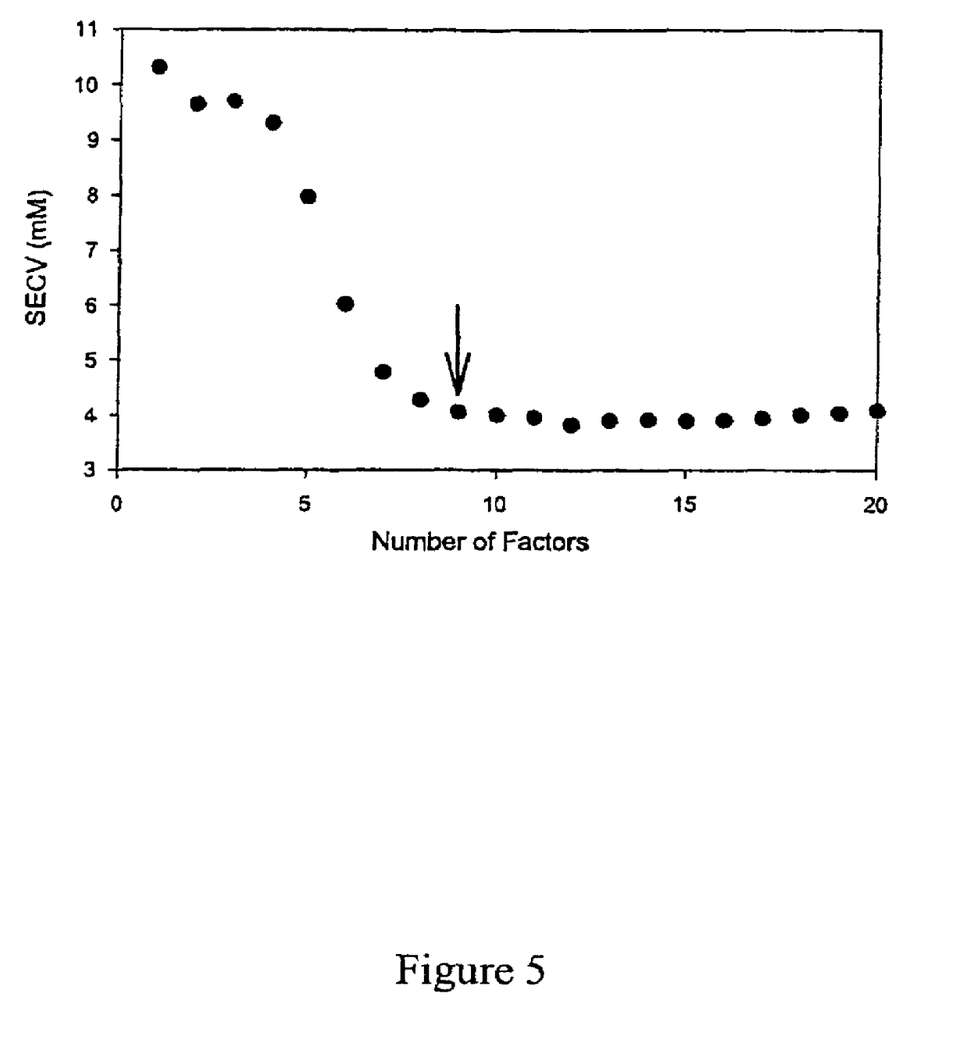
FIG. 5 shows the standard error of cross-validation vs. the number of factors used to build the partial least squares calibration model of Example 3.

A partial least squares regression calibration model was generated from the data collected in the foregoing experiment. A set of 54 randomly selected spectra were removed from the data set and set aside for an independent measure of the standard error of prediction after the calibration was constructed. All remaining spectra, (approximately 306) were used to build the partial least squares calibration model. The number of factors was chosen by performing 50 repetitions of a randomly selected leave-one-third-out cross validation of the calibration spectra after mean centering. The average standard error of cross validation (SECV) from the 50 repetitions is shown in FIG. 5. From the SECV, nine factors were determined as defining the optimal subspace.

The resulting PLS calibration spectrum is depicted on FIG. 5 as the solid line, along with the pure component absorption spectrum for glucose. As illustrated, there was little high-frequency noise-like structure in the PLS calibration spectrum. However, there was only a vague similarity between the PLS calibration spectrum and the pure component spectrum for glucose. More specifically, the PLS model was generated using a conventional blind regression of factors in order to establish a correlation with the concentration of glucose in the lab rat. The PLS calibration is indicated as the dashed line in FIG. 5.

Figure 6:
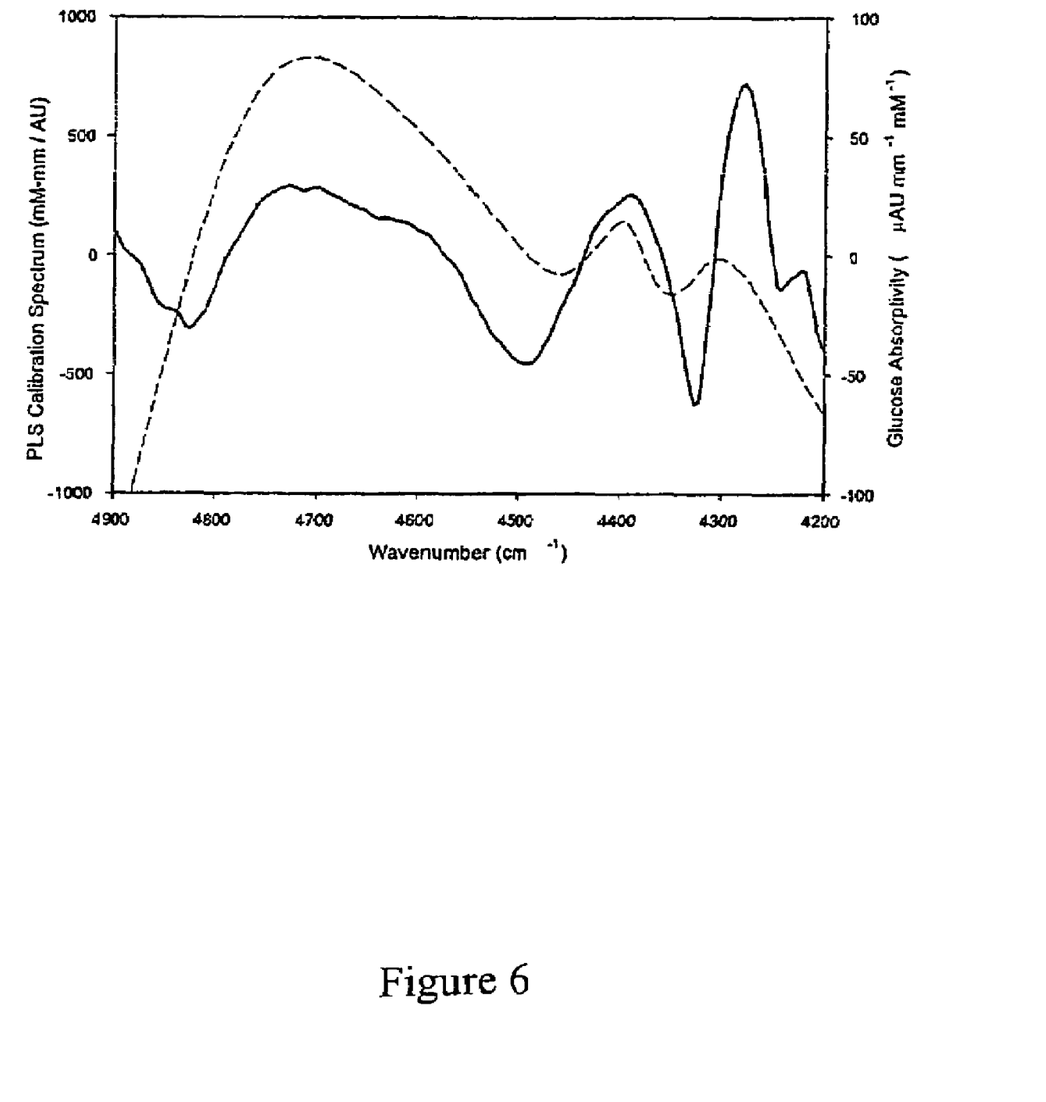
FIG. 6 shows a calibration spectrum generated by the partial least squares model of Example 3 compared to the pure component spectrum of glucose.

The results of applying the PLS calibration model to the in vivo spectra are shown in FIG. 6. The modeled concentrations for spectra used to build the calibration model are depicted as open circles while those for the independent prediction set are shown as solid circles. The solid line shows the glucose concentrations of blood samples taken from the arterial line.

The correlation between the modeled concentration and those determined from the arterial blood samples shows a good agreement with the exception of the period from 13:00-13:45 during which time the optical fiber interface was repositioned between in vivo spectra. Once again, during the period of elevated glucose, the modeled glucose concentrations appear to lag behind the arterial samples by approximately 15-20 minutes, which is to be expected due to the time required for arterial glucose to propagate to the intracellular and intercellular spaces.

In analyzing this PLS calibration model, even though there appears to be an analytically significant correlation between the arterial glucose and the predicted concentrations obtained by the PLS regression method, it is not certain that the correlation is a result of glucose spectral information and not secondary effects or chance correlations.

EXAMPLE 4

Generation of Synthetic PLS Multivariate Calibration Spectrum

Figure 7:
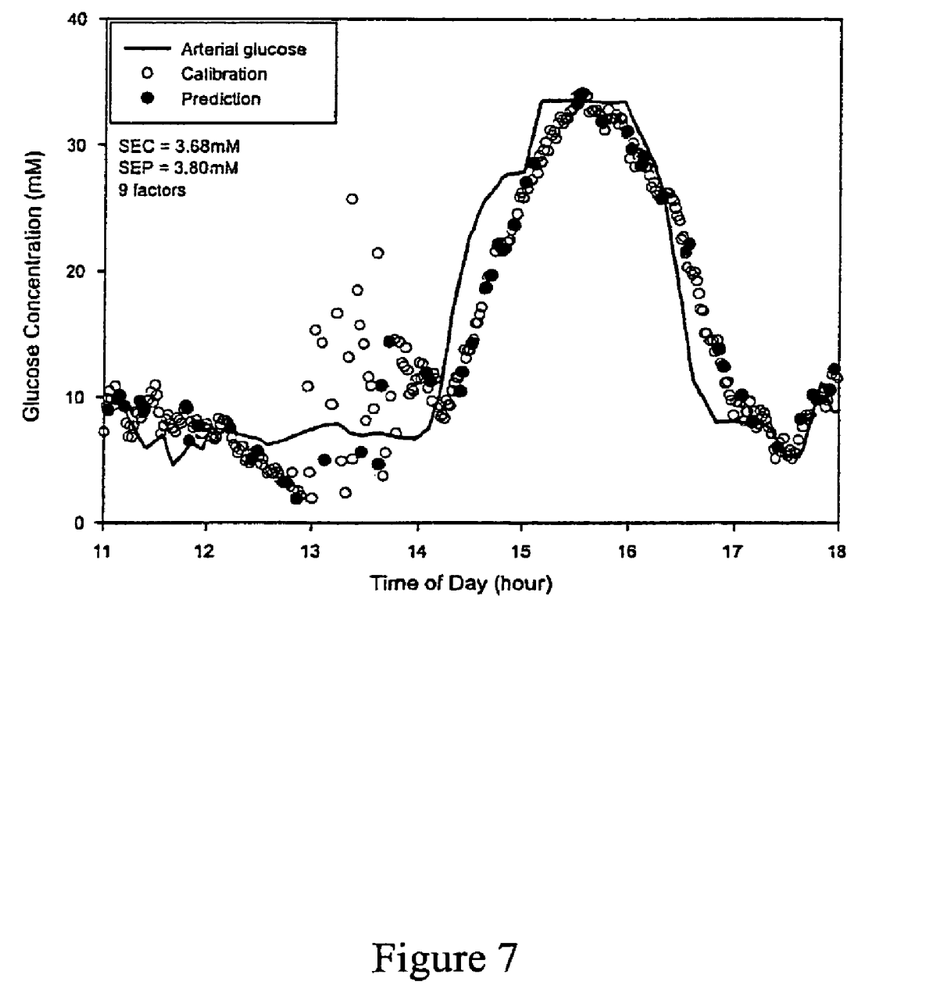
FIG. 7 shows the predicted glucose concentrations using the partial least squares calibration model of Example 3.

A synthetic partial least squares calibration model was generated in a similar manner to the in vivo PLS model. First, the synthetic PLS model was constructed from synthesized spectra based upon the regressions of the tissue spectra in terms of the major tissue components. Each synthesized spectrum was a linear combination of the spectra associated with water, glucose, collagen, keratin, fat, a constant spectrum, and a spectrum representing the temperature dependence of water. The amount of each component was determined by the regression coefficients from the fitted in vivo spectra. The results of the synthetic PLS calibration model are illustrated in FIG. 7 along with the PLS calibration spectra generated from the in vivo spectra. As indicated, the two calibration models are very similar in their dominant spectral features.

EXAMPLE 5

Figure 8:
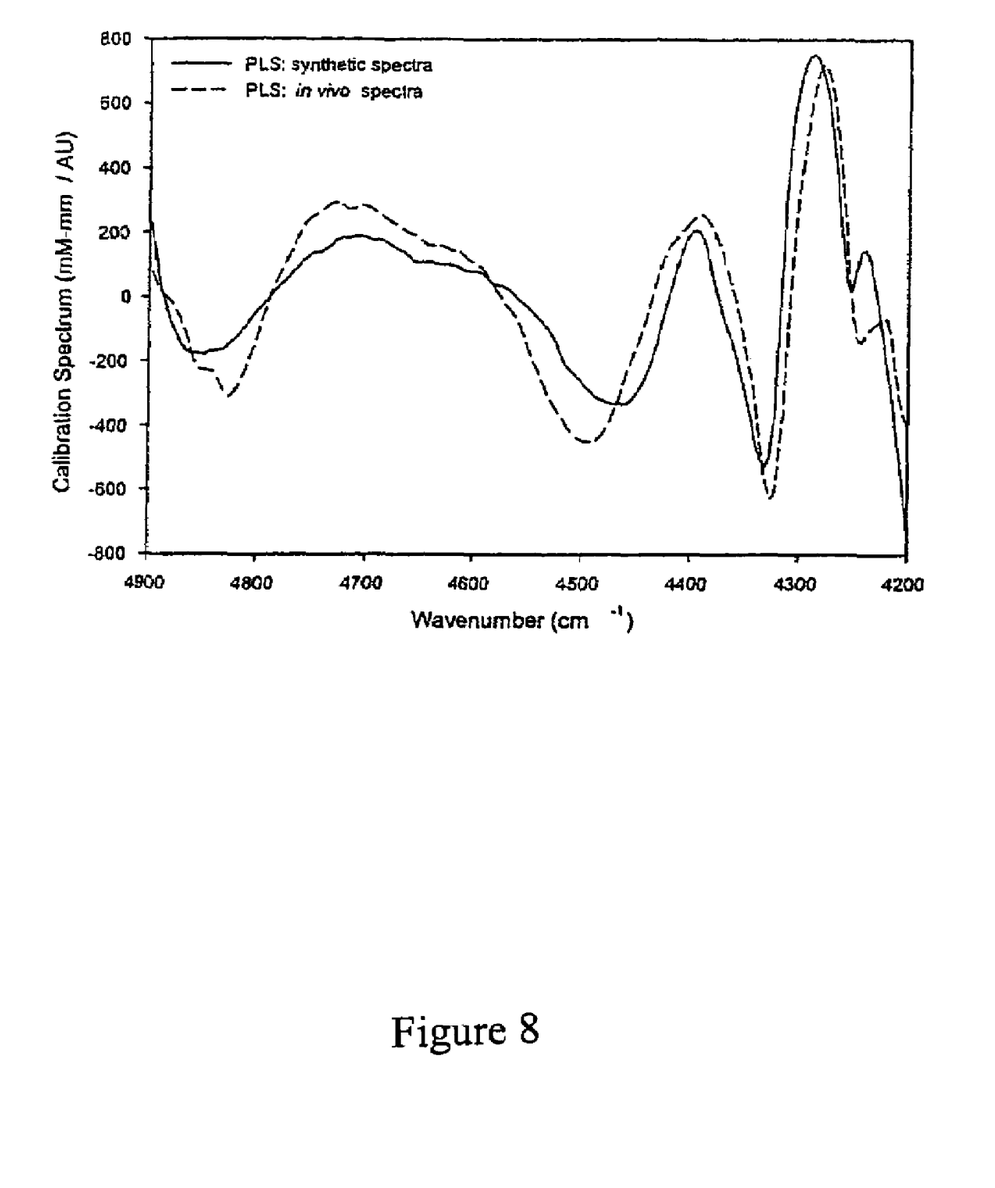
FIG. 8 shows a direct comparison of the synthetic partial least squares calibration model of Example 4 with the in vivo partial least squares calibration model of Example 3.
Figure 9:
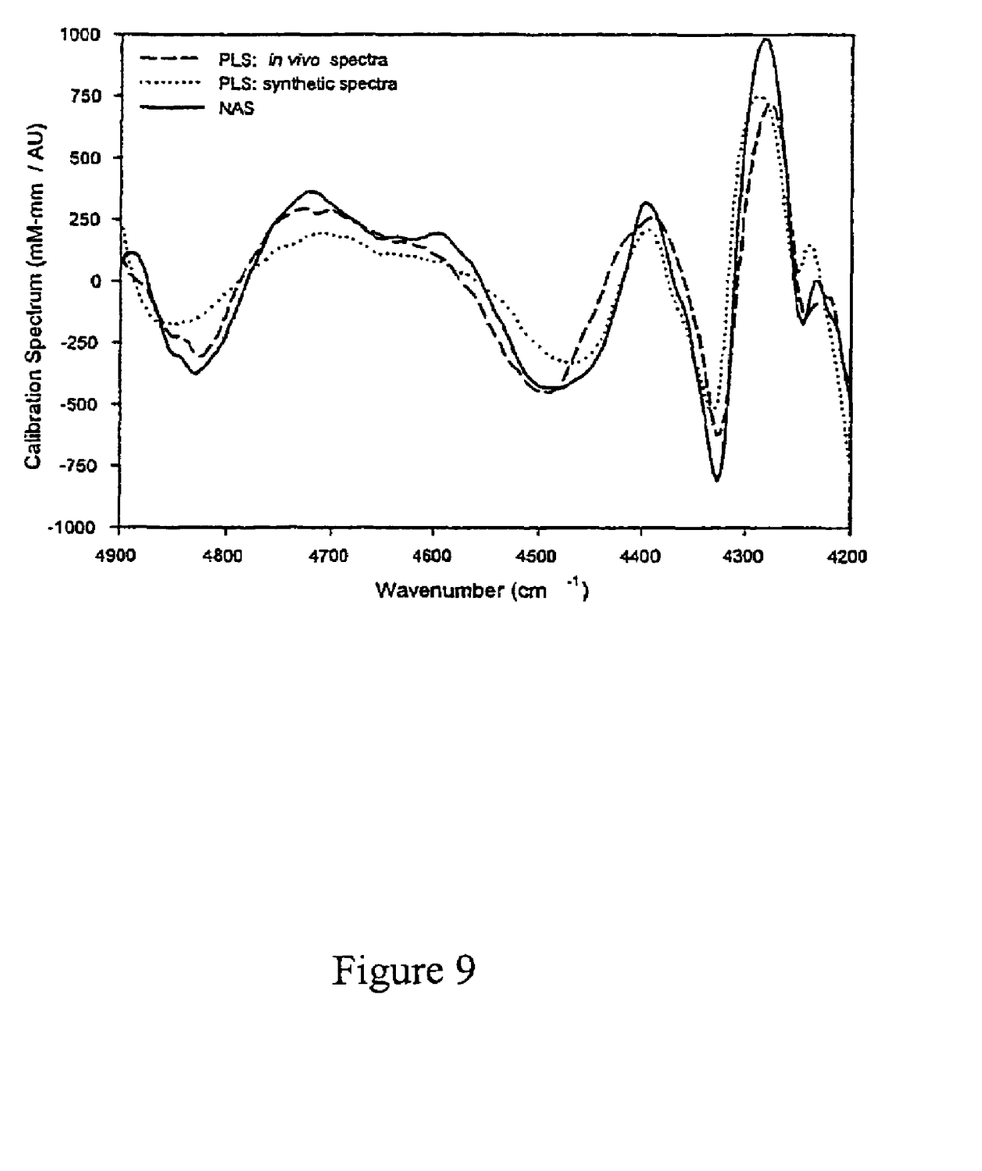
FIG. 9 shows a comparison of the net analyte signal calibration vector of Example 1 with the partial least squares calibration vectors of Examples 3 and 4.

Use of Net Analyte Signal Calibration Vector to Verify the Analytical Significance of the Statistical Multivariate Calibration Models Obtained from Partial Least Squares Analysis of in vivo Spectra The net analyte signal calibration vector obtained from Example 1 was directly compared to the PLS calibration vectors generated in Examples 3 and 4. The results are indicated on FIG. 8. As illustrated, the dominant features of all three calibrations analytically agree in shape and amplitude. Thus, the net analyte signal calibration model, which was derived from glucose specific absorption features present in in vivo spectra, can be used to provide evidence that the PLS calibration models do in fact correlate to glucose specific spectral features.

In view of the foregoing, it will be apparent to those skilled in the art that various modifications and variations can be made in the present invention without departing from the scope or spirit thereof. As such, other aspects of the present invention will become apparent to those skilled in the art from consideration of the instant specification and practice of the invention disclosed herein.

What is claimed is:

1. A method for generating a net analyte signal calibration model for use in detecting an analyte in a test subject, comprising:
   a) providing a set of in vivo infrared spectra for a test subject during a period in which an analyte concentration is essentially constant;
   b) calculating an optimal subspace of spectra that at least substantially describes all non-analyte dependent spectral variance in the in vivo spectra of step a);
   c) providing a pure component infrared spectrum for the analyte; and
   d) calculating a net analyte signal spectrum from a data set comprising the optimal subspace spectra of b) and the pure analyte spectrum of c), wherein the net analyte signal spectrum identifies one or more in vivo spectral features specific to the analyte.

2. The method of claim 1, wherein the spectra are absorption spectra.

3. The method of claim 2, wherein the absorption spectra are near infrared absorption spectra in the range of from approximately 4000 cm$^{-1}$ to approximately 5000 cm$^{-1}$.

4. The method of claim 2, wherein the absorption spectra are near infrared absorption spectra in the range of from approximately 5500 cm$^{-1}$ to approximately 6500 cm$^{-1}$.

5. The method of claim 1, wherein the spectra are reflectance spectra.

6. The method of claim 1, wherein the spectra are single-beam spectra.

7. The method of claim 1, wherein the infrared spectra are absorption spectra in the mid infrared spectral range.

8. The method of claim 7, wherein the absorption spectra are in the range of from approximately 1200 cm$^{-1}$ to approximately 900 cm$^{-1}$.

9. The method of claim 1, wherein the analyte is a physiological chemical.

10. The method of claim 9, wherein the analyte is glucose, urea, lactate, triglyceride, total protein, cholesterol, or ethanol.

11. The method of claim 9, wherein the physiological chemical comprises at least one C—H, N—H, or O—H molecular bond.

12. The method of claim 9, wherein the analyte is glucose.

13. The method of claim 1, wherein the test subject is a living organism.

14. The method of claim 13, wherein the test subject is a plant.

15. The method of claim 13, wherein the test subject is an animal.

16. The method of claim 15, wherein the animal is non-mammalian.

17. The method of claim 15, wherein the animal is mammalian.

18. The method of claim 13, wherein the test subject is a microbial species.

19. The method of claim 13, wherein the test subject is a human.

20. The method of claim 1, wherein step b) comprises a principle component analysis.

21. The method of claim 1, further comprising reporting the net analyte signal calibration spectrum on a display device.

22. The method of claim 1, further comprising storing the net analyte signal spectrum on a recordable medium.

23. A method for non-invasively measuring the concentration of an analyte in a test subject, comprising:
   (a) identifying a test subject in need of having an analyte concentration measured;
   (b) generating an in vivo net analyte signal calibration model by:
      i) providing a set of in vivo infrared spectra for a test subject during a period in which an analyte concentration is essentially constant;
      ii) calculating an optimal subspace of spectra that at least substantially describes all non-analyte dependent spectral variance in the in vivo spectra of step i);
      iii) providing a pure component infrared spectrum for the analyte; and iv) calculating the net analyte signal spectrum from a data set comprising the optimal subspace spectra of ii) and the pure analyte spectrum of iii), wherein the net analyte signal spectrum identifies one or more in vivo spectral features specific to the analyte;

(c) providing an in vivo infrared spectrum of the test subject; and (d) calculating a predicted concentration of the analyte in the test subject from a data set comprising the net analyte signal calibration model and the in vivo infrared spectrum of the test subject.

24. The method of claim 23, wherein the analyte is a physiological chemical.

25. The method of claim 24, wherein the analyte is glucose, urea, lactate, triglyceride, total protein, cholesterol, or ethanol.

26. The method of claim 25, wherein the analyte is glucose.

27. The method of claim 23, wherein the test subject is any living organism.

28. The method of claim 27, wherein the test subject is a plant.

29. The method of claim 27, wherein the test subject is a mammal.

30. The method of claim 27, wherein the test subject is a human.

31. The method of claim 23, further comprising reporting the predicted concentration on a display device.

32. The method of claim 23, further comprising storing the predicted concentration on a recordable medium.

* * * * *